United States Patent [19]

Herrmann

[11] Patent Number: 5,429,694

[45] Date of Patent: Jul. 4, 1995

[54] APPARATUS AND METHOD FOR APPLYING TENSIONED ELASTIC TO MATERIAL

[75] Inventor: Thomas R. Herrmann, Federal Way, Wash.

[73] Assignee: Paragon Trade Brands, Inc., Federal Way, Wash.

[21] Appl. No.: 222,969

[22] Filed: Apr. 5, 1994

[51] Int. Cl.⁶ ............................................ A61F 13/15
[52] U.S. Cl. ................................. 156/164; 156/161; 156/229; 156/494; 156/496; 156/439; 156/552
[58] Field of Search ............... 156/160, 161, 163, 164, 156/229, 496, 494, 552, 556, 439, 436; 604/385.2

[56] References Cited

U.S. PATENT DOCUMENTS

| | | |
|---|---|---|
| 3,728,191 | 4/1973 | Wierzba et al. |
| 4,242,167 | 12/1980 | Hoffmann |
| 4,284,454 | 8/1981 | Joa |
| 4,394,933 | 7/1983 | Ackley |
| 4,523,969 | 6/1985 | Spencer |
| 4,608,115 | 8/1986 | Schroth et al. |
| 4,642,151 | 2/1987 | Coenen |
| 4,726,874 | 2/1988 | Van Vliet |
| 4,735,673 | 4/1988 | Piron ....................... 156/229 X |
| 4,776,911 | 10/1988 | Uda et al. |
| 4,786,346 | 11/1988 | Ales et al. |
| 4,925,520 | 5/1990 | Beaudoin et al. ............. 156/229 |
| 4,943,340 | 7/1990 | Ujimoto et al. ............. 156/229 X |
| 5,000,806 | 3/1991 | Merkatoris et al. |
| 5,043,036 | 8/1991 | Swenson |
| 5,308,345 | 5/1994 | Herrin ........................ 604/385.2 |

Primary Examiner—Jeff H. Aftergut
Attorney, Agent, or Firm—Klarquist, Sparkman, Campbell, Leigh & Whinston

[57] ABSTRACT

Apparatus for applying tensioned elastic to material including a first conveyor for carrying material in one direction along a flow path, a second conveyor operable to draw elastic from a storage container, tension the elastic, and move the elastic longitudinally in a tensioned state along a region extending transversely of and spaced from the first conveyor flow path, and a pair of transfer grippers. The transfer grippers are movable along a path in the direction of the flow path and are positioned to grasp spaced regions of elastic held by the second conveyor. Cutters are positioned laterally outwardly of the grippers to sever elastic from the second conveyor after being grasped by the grippers. The grippers maintain the elastic in a tensioned condition and deposit on the material. Also disclosed is a method for applying tensioned elastic to material, generally as described above in relation to the apparatus.

30 Claims, 6 Drawing Sheets

APPARATUS AND METHOD FOR APPLYING TENSIONED ELASTIC TO MATERIAL

BACKGROUND AND SUMMARY OF THE INVENTION

The present invention relates to apparatus and method for applying tensioned elastic to material, and more specifically to apparatus and method for applying elongate tensioned elastic members transversely to a moving web of material.

The application of elongate tensioned elastic extending transversely of a moving flow path has been difficult to accomplish with previously known apparatus and methods. Many previously known devices and methods have used apparatus which requires that the apparatus stop, or slow down substantially, and then start, or speed up, again to permit transference of the elastic onto material. Other methods and equipment may include the application of non-tensioned material in a substantially continuous stream which then must be further acted upon, such as by heat activation or other process, to produce an elastic characteristic in the material. Yet others use apparatus and methods which may provide adequate operation for applying tape-like materials, but are less desirable for applying tensioned elastic strands.

A general object of the present invention is to provide novel apparatus which permits substantially continuous movement of elongate elastic from an elastic storage to final application on material, with the tensioned elastic extending transversely of the flow path of the material on which it is to be applied.

More specifically, an object of the invention is to provide apparatus in which material to have elastic applied thereto is carried in one direction along a flow path, and a conveyor extending transversely of the material flow path is operable to continuously draw elastic from storage, tension it and carry it into a position extending transversely of and spaced from the material flow path. A transfer conveyor movable generally in the direction of the flow path is operable to grip a section of the elastic extending transversely of the flow path, and a severing device is operable to sever the elastic outside the grip of the transfer conveyor allowing the transfer conveyor to carry a selected length of elastic into position to be deposited on the material. The transverse conveyor and the transfer conveyor are able to operate substantially continuously to produce substantially continuous material movement.

Another object of the present invention is to provide novel apparatus in which elongate tensioned elastic can be substantially continuously provided extending transversely of a moving web of material which may be used to produce a garment. The apparatus is suitable for application of elastic at high working speeds without the need for interruption or intermittent operation of the moving web of material used to produce the garment. It is especially well adapted for the application of the waist zone elastics to disposable diapers or similar products. A first conveyor is operable to carry garment material in one direction along a flow path. A second, or transverse, conveyor extends transversely of the flow path and is operable to draw an elongate section of elastic from an elastic storage, impart tension to the elastic, and carry it substantially continuously into a position extending transversely of and spaced from a web of material carried along the flow path. A pair of spaced apart transfer grippers are carried in the direction of the material flow path and are operable to grasp spaced portions of the elastic carried on the transverse conveyors. Substantially immediately after being grasped portions of the elastic outside the spaced transfer grippers are severed from remainder portions of the elastic held in the transverse conveyor, permitting the transfer grippers to carry stretched elastic extending transversely of the material path into a position to deposit it on the material web.

Another object of the invention is to provide a novel method for applying elongate tensioned elastic to material moving in one direction along a flow path with the elastic extending transversely of the flow path. The method includes the steps of drawing an elongate section of elastic from a quantity of elastic, stretching the section of elastic to a desired tension, moving the elastic in its tensioned state longitudinally and substantially continuously along a second flow path extending transversely of and spaced from the flow path for the material, grasping spaced apart portions of the section of elastic adjacent opposite sides of the flow path, and while maintaining tension in the elastic moving it in the direction of the material flow path, cutting the section of elastic outside the spaced portions to sever the elastic from remainder portions drawn from the elastic storage, and depositing the severed elastic while still in tension on material carried along the flow path.

These and other objects and advantages will become more apparent as the following description is read in conjunction with the drawings.

DESCRIPTION OF PREFERRED EMBODIMENTS OF THE INVENTION

Figure 1:
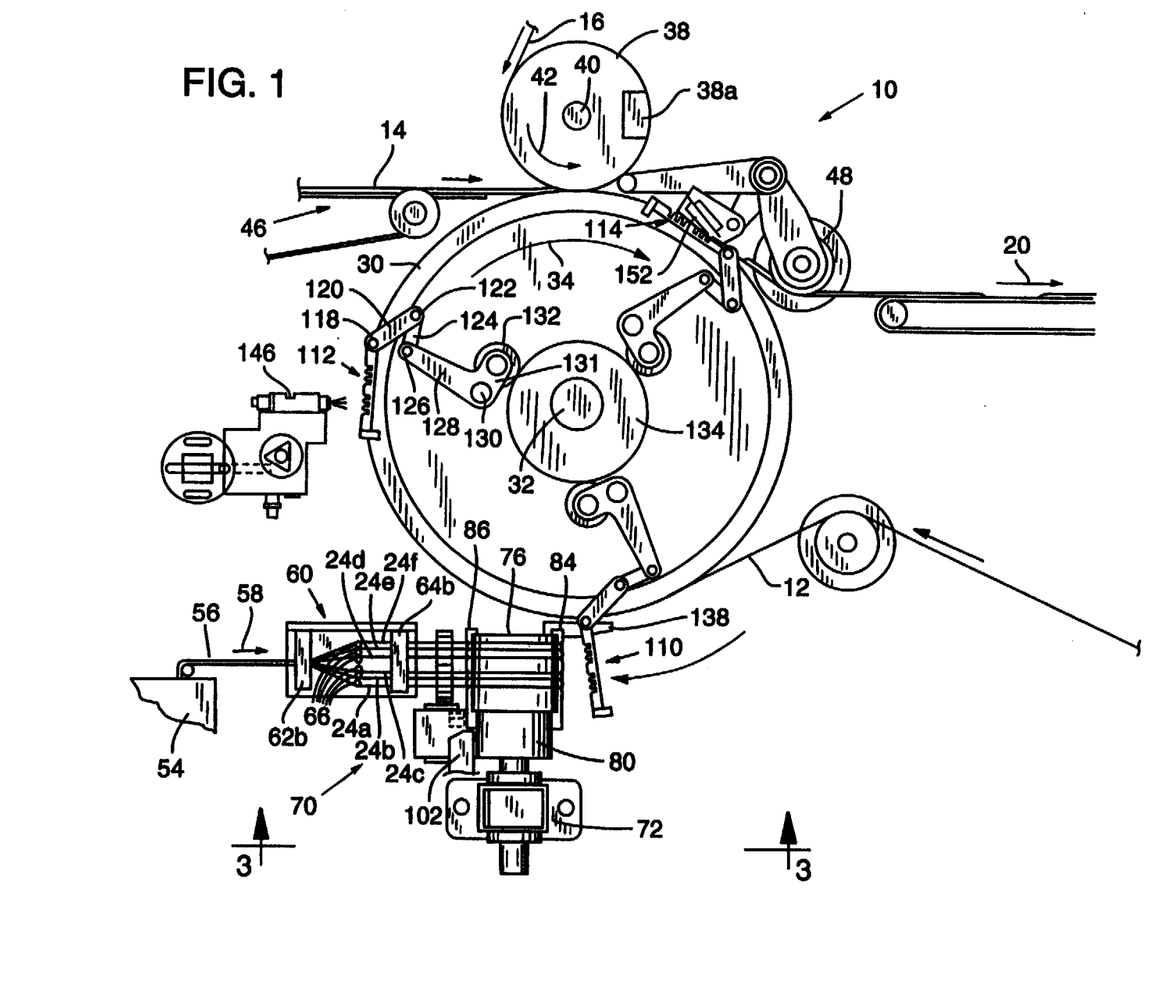
FIG. 1 is a side elevation view of apparatus constructed according to an embodiment of the invention in which the method of the invention is practiced.
Figure 2:
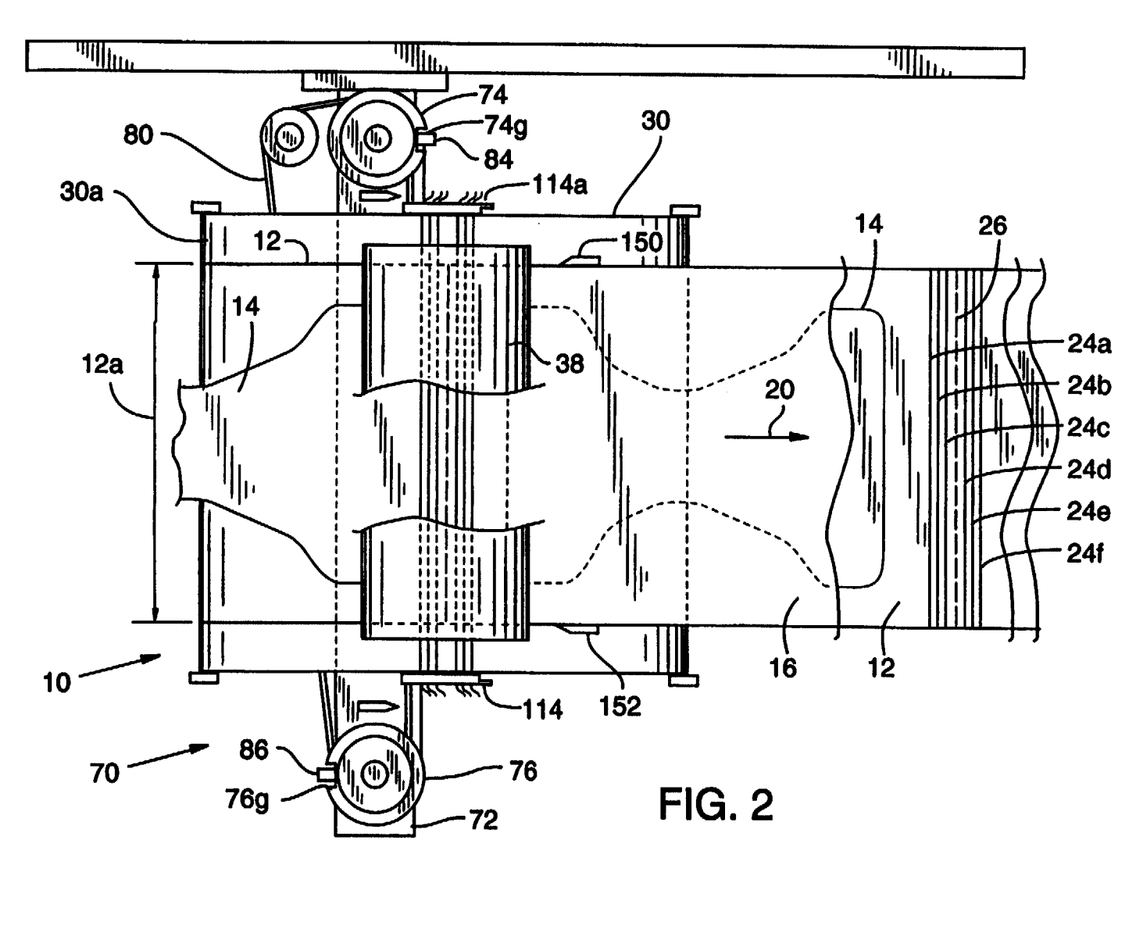
FIG. 2 is a top plan view of the apparatus illustrated in FIG. 1.

Referring first to FIGS. 1 and 2, at 10 is indicated generally apparatus constructed according to an embodiment of the invention. The apparatus is illustrated specifically in use to produce disposable diapers or training pants, but it should be understood that it is not limited to such products.

As is known, disposable diapers and training pants generally include an outer, or backing, sheet of a liquid impervious material, onto which an absorbent pad is placed. A liquid pervious liner, or inner, sheet is placed thereon to encase the absorbent pad therebetween. One such garment and method of manufacture is illustrated in U.S. Pat. No. 4,726,807 to Young and Lancaster, which is herein incorporated by reference to illustrate typical materials used and known methods of manufacturing such garments.

In the manufacture of such products it is often desirable to be able to provide strands, or bands, of elastic material extending transversely of the inner and outer sheets to produce elasticized waist areas for the garment produced. Since such products often are manufactured on assembly lines in which the garment material moves substantially continuously longitudinally, in what is referred to as the "machine direction", the elastic must be placed on a moving web with the elastic stretched and extending transversely of the machine direction.

Referring to FIGS. 1 and 2, an elongate sheet, or web, of backing material 12 having a selected width is moved in one direction along a flow path. An elongate absorbent pad 14 is placed thereon, and an elongate sheet of inner liner material 16 is laid thereover. As is seen in FIG. 2, the material is carried in a flow path direction 20 which is generally longitudinally, or in a machine direction, for the garments to be produced.

For example, the liquid impervious back sheet 12 may be a thin thermoplastic material, such as a pigmented polyethylene film having a thickness in the range of 0.02–0.04 mm. The liquid pervious liner sheet 16 may be a carded polyester fiber with a latex binder or of a spunbonded polypropylene having continuous fibers and thermally bonded by patterned calendar rolls. The liner sheet may be impregnated with a surfactant to render it hydrophilic. The moisture absorbent layer, or pad, 14 may be of wood fibers or other fibers, such as chemical wood pulp, or any other suitable liquid absorbing material such as commercially available fluff pulp or a fluffed bleached craft soft wood pulp.

A series of elongate elastic elements 24, herein shown as individual elastic bands 24a, 24b, 24c, 24d, 24e, 24f extend transversely of the flow path 20 and are adhered to backing material 12. A dashed line 26 (see FIG. 2) positioned between the three elastic bands 24a, 24b, 24c and the other three bands 24d, 24e, 24f indicates a transverse cut-off line at which one garment will be severed from the following garment in the manufacturing process. The elastic bands provided will serve to elasticize the waist regions of garments produced.

Describing the apparatus, and referring still to FIGS. 1 and 2, it includes a circular conveying drum 30 which is supported on and driven about a central axle 32. The direction of rotation is indicated generally by arrow 34. The peripheral outer surface 30a of the drum supports backing material 12 as it travels from the bottom side of the drum to the top side of the drum in FIG. 1. As is seen in FIG. 2, the drum is wider than the usual width of material to be carried thereon so that it can accommodate sheet material of different widths.

An elongate upper drum 38 is mounted for powered rotation on an axle 40 substantial parallel to axle 32 in the direction indicated by arrow 42. Drum 38 has an external contour which will not substantially compress absorbent pad 14, but does have a bumper section 38a extending substantially fully across the length of drum 38 which presses materials tightly between drum 38 and drum 30. This, as will be discussed later, serves to press the backing and liner material tightly together over elastic bands 24a, 24b, 24c, 24d, 24e, 24f.

Drum 38 carries liner sheet material 16 into position adjacent and overlying backing material 12 and pads 14.

A pad conveyor 46 is operable to carry longitudinally spaced pads 14 and insert them into the space between backing sheet 12 and liner sheet 16, such that a pad will be carried by the backing and liner sheets through the nip between rollers 30, 38 and be captured between the two sheets. The spacing between longitudinally moving pads 14 is such that they are positioned between elastic bands which are deposited on backing material 12.

The combined backing and liner sheet with an absorbent pad encased therebetween are carried downstream, to the right in FIGS. 1 and 2, and are supported on a subsequent roller 48, and other conveyor mechanism in the system as they are moved therealong.

Referring now more specifically to the apparatus for applying elastic strands and referring to FIG. 1, an elastic storage container is indicated generally at 54. An elongate strip of elastic material 56 is drawn from container 54 and carried in the direction of arrow 58. The elastic strip material already has been scored during its manufacture such that it is easily split into the multiple elastic bands, or strands, such as those noted at 24a, 24b, 24c, 24d, 24e, 24f.

An example of the elastic used is 0.015 inch by 0.027 inch three end natural rubber obtained from Fulflex. However, the elastic may be any form of elasticized material which may be found to be desirable for producing the product at hand. Examples of other materials which might be used are polyurethane, ribbon elastic, lycra strands, or others used in the industry.

Figure 3:
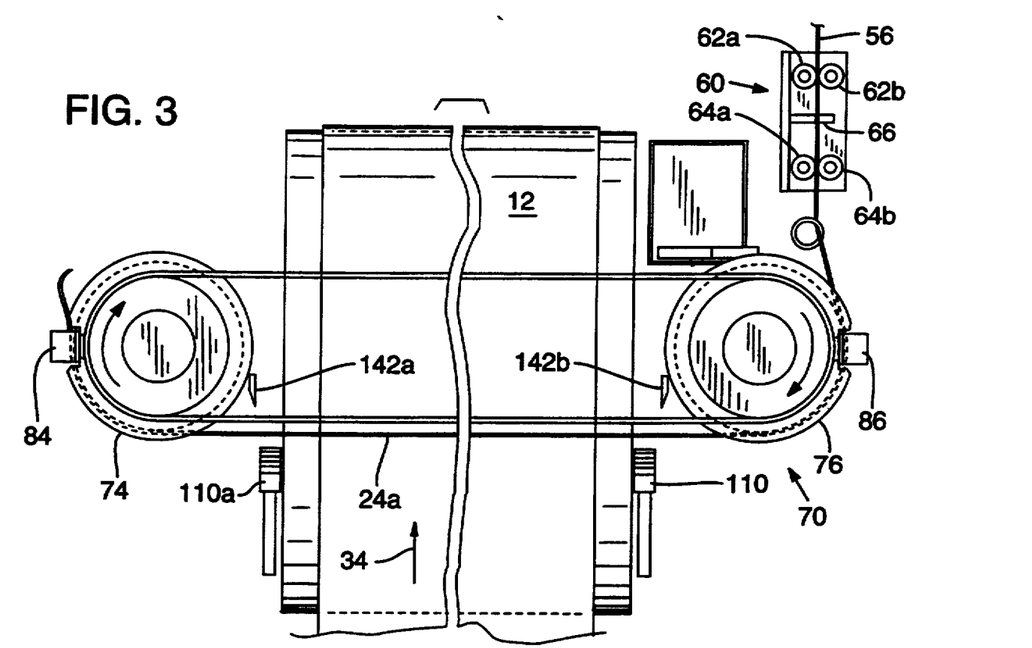
FIGS. 3 and 3A are views taken generally along the line 3—3 in FIG. 1.

A splitter device which separates the scored elastic strip into multiple strands and also provides initial tensioning of the strands is indicated generally at 60 (See FIGS. 1 and 3). This splitter device includes a first pair of rollers 62a, 62b positioned one above the other, between the nip of which strip 56 is moved. A second set of powered rollers 64a, 64b are positioned one above the other and downstream from rollers 62 with the elastic bands extending through the nip between rollers 64a, 64b. Rollers 64a, 64b are driven at a speed greater than rollers 62a, 62b, such that tension is imparted to the elastic bands and they are stretched to a desired degree. A plurality of spaced pins 66 are disposed intermediate rollers 62, 64 with the elastic bands being routed about the pins to separate strip 56 into six individual bands 24a–24f.

Underlying drum 30 is an elastic band transverse conveyor indicated generally at 70. Further details of this transverse conveyor are found in FIGS. 2–7.

Figure 4:
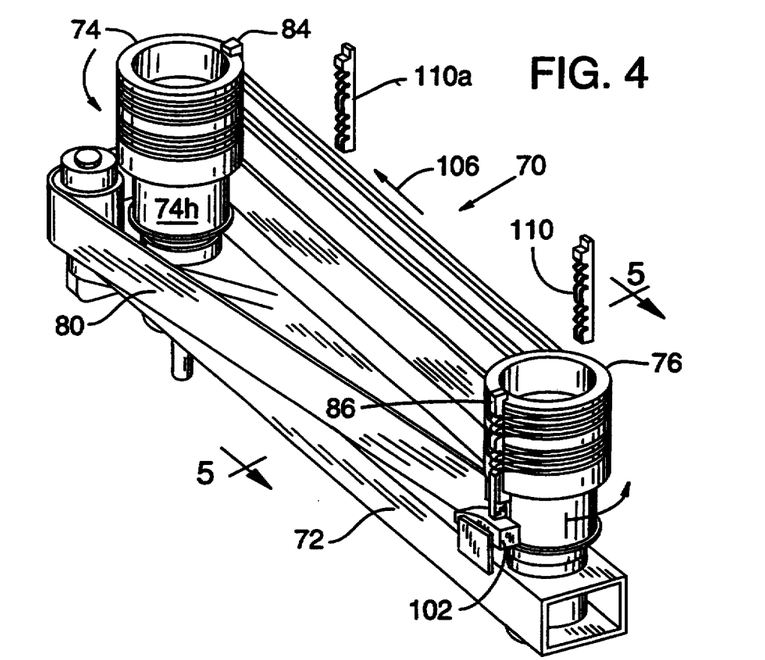
FIG. 4 is an enlarged perspective view of elastic conveyor mechanism removed from the apparatus for clarity and illustration.

Referring to FIG. 1, 2 and 4 an elongate support beam 72 extends substantially horizontally and transversely under drum 30. A pair of spaced apart guide drums 74, 76 are mounted on power driven, substantially upright shafts rotatably mounted on beam 72.

Figures 5, 6, 7:
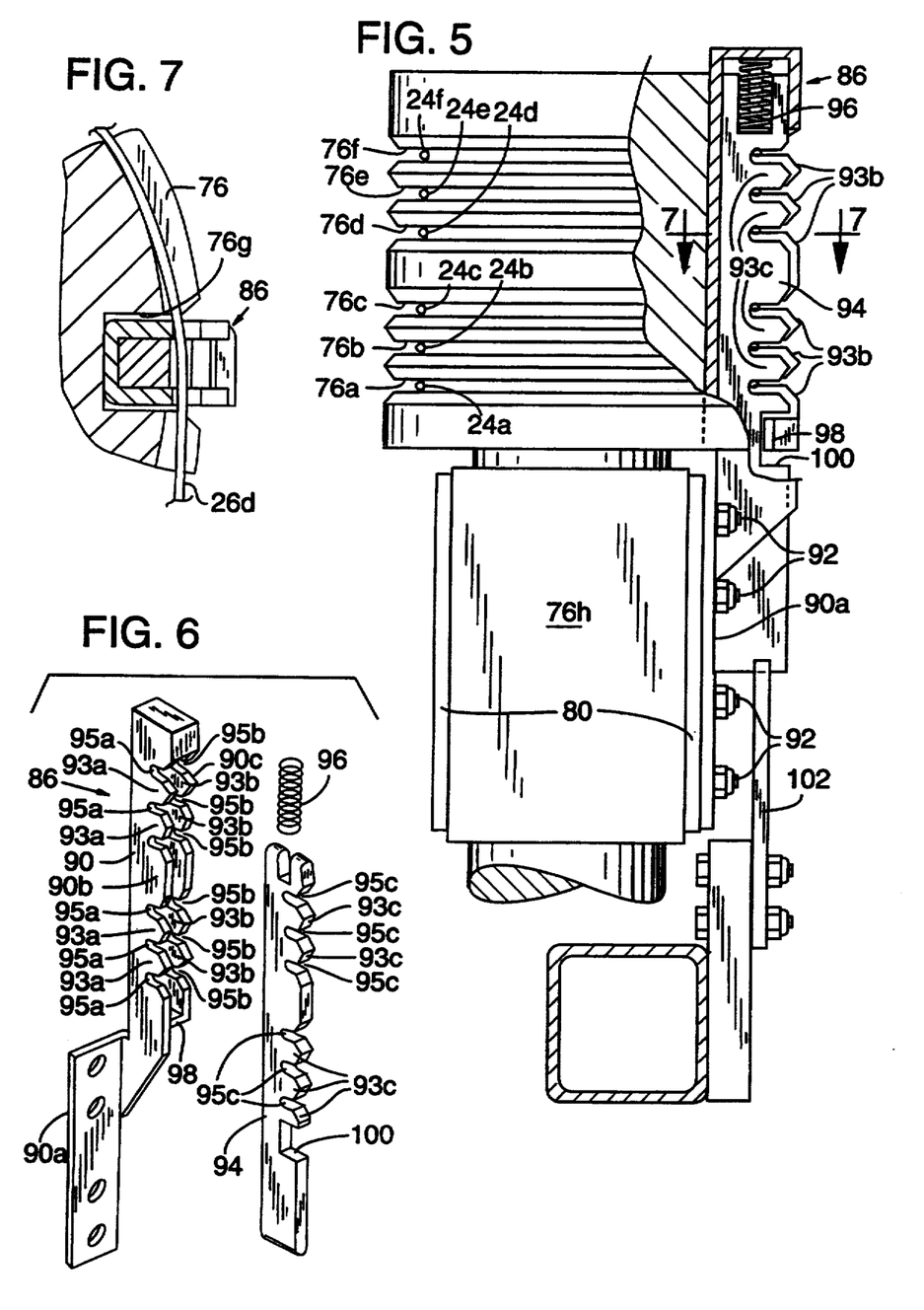
FIG. 5 is an enlarged view taken generally along the line 5—5 in FIG. 4.
FIG. 6 is an exploded perspective view of an elastic gripper illustrated in FIG. 5.
FIG. 7 is an enlarged cross-sectional view taken generally along the line 7—7 in FIG. 5.

Referring to FIGS. 1, 2 and 5, each of drums 74, 76 has a plurality of circumferential grooves, such as those indicated at 76a, 76b, 76c, 76d, 76e, 76f, formed therein. These grooves in drums 74, 76 are adapted to receive and guide individual elastic bands such as those indicated at 24a–24f held in the grooves in FIG. 5.

Referring to FIGS. 2 and 7, each of drums 74, 76 has an elongate upright recess 74g, 76g defined therein for receiving an elastic gripping device as will be further defined below.

Referring still to FIGS. 1, 2, 4 and 5, each of drums 74, 76 has a necked down lower portion 74h, 76h about which is trained an elongate endless, flexible timing belt 80.

Secured at spaced apart locations on the timing belt 80 are a pair of toothed lock blocks, or grippers, 84, 86.

Referring to FIGS. 5–7, it will be seen that a lock block includes an elongate channel member 90 having an extension 90a with bores extending therethrough. Attaching bolts, such as those indicated at 92, may extend through the bores in extension 90a to secure the lock block to timing belt 80. The lock block extends upwardly from timing belt 80 and maybe received in grooves 74g, 76g of drums 74, 76 as it travels with belt 80.

The channel member 90 has a pair of substantially parallel, laterally spaced elongate side portions 90b, 90c. Side portions 90b, 90c have aligned tooth-like projections 93a, 93b formed thereon which define elastic receiving grooves 95a, 95b therebetween.

An elongate substantially planar locking member 94 fits slidably between side portions 90b, 90c and has teeth 93c and grooves 95c therein substantially matching the teeth and grooves of side portions 90b, 90c. An elongate compression spring 96 interposed between a top portion of channel member 90 and the top of member 94 urges member 94 downwardly relative to member 90. A bent-over portion 98 of sidewall portion 90c is received within an elongate notch 100 in member 94 to limit vertical movement of member 94 relative to member 90.

In FIG. 5, members 90, 94 are illustrated in what is referred to herein as a locking position with elastic bands 24a–24f captured in individual spaces between the teeth of the members of the lock block. Spring 96 presses downwardly on member 94 to lock the bands therein. Member 94 also is shiftable upwardly against the biasing force of spring 96, whereby the grooves between adjacent teeth on member 94 are substantially aligned with the grooves between adjacent teeth on member 90 to unlock the elastic strands, or bands, to allow the entry or exit of bands therein.

Referring still to FIGS. 4 and 5, a somewhat wedge-shaped cam block 102 is provided adjacent drum 76. The upper surface of cam 102 inclines upwardly on progressing toward the drum. As a lock block, which is usually in its closed, or locked position as illustrated in FIG. 5, is moved to the region of cam 102, the lower end of element 94 rides up on the ramped upper surface of the cam which causes member 94 to shift upwardly to open the grooves between the teeth. In this position the grooves are opened to receive strands 24a–24f delivered thereto by splitter 60. After the strands are received in the grooves of the lock block, the lock block is moved by the timing belt past the end of cam 102 and member 94 is urged downwardly by spring 96 to lock the strands therein.

In FIGS. 2 and 4, lock block 84 already has captured, and holds a region of the elastic strands. Movement of lock block 84 with the timing belt in the direction of arrow 106 has drawn the elastic bands into and around the peripheral grooves in drum 76 and a reach, or region, of the bands spans the distance between drums 74, 76.

Lock block 86, being operated upon by wedge cam 102 is opened to receive elastic bands from splitter 60. As lock block 86 travels with timing belt 80 around drum 76 it will carry portions of the elastic strands received from splitter 60 into the peripheral grooves omits associated drum to maintain alignment of the strands.

The reaches, or regions, of elastic strands extending between lock blocks 84, 86 as illustrated in the figures are tensioned and carried in their tensioned state in the direction of arrow 106 transversely of and spaced somewhat outwardly from the periphery of drum 30 and the path of backing material carried about the drum. The strands extending between drums 74, 76 are aligned in a plane extending generally radially outwardly from drum 30.

Referring again to FIG. 1, a plurality of transfer conveyor lock blocks, or grippers, 110, 112, 114 are mounted at one end of the drum and are spaced apart circumferentially about the drum.

A similar set of transfer lock blocks, or grippers, are mounted at the opposite end of drum 30 as indicated at 114a in FIG. 2. This opposite set of transfer conveyor lock blocks are directly aligned with lock blocks 110, 112, 114 at the opposite end of the drum.

Each of the transfer lock blocks is similarly mounted and actuated, and thus only transfer lock block 112 will be described in detail. Referring to FIG. 1, lock block 112 is pivotally connected at 118 to drum 30, permitting it to swing from a position as illustrated for lock block 112, extending substantially tangent to the periphery of the drum, to a position as illustrated for lock block 110 extending substantially radially outwardly from the drum.

A connector link 120 is secured to lock block 112 adjacent pivot 118. The opposite end of link 120 is pivotally connected at 122 to an intermediate link 124. The opposite end of intermediate link 124 is pivotally connected at 126 to one leg of a bell crank 128 which is pivotally connected at 130 to the drum. The angularly disposed shorter leg 131 of bell crank 128 has a roller 132 rotatably mounted thereon which rolls along the peripheral surface of a stationary eccentric cam 134. Rotation of the drum with the lock blocks and their attendant operating mechanism rotating about cam 134 causes the lock blocks to swing between first, or depositing, positions extending substantially tangent to the periphery of the drum as indicated for lock blocks 112, 114, and a second, or pick up position, extending radially outwardly from the periphery of the drum as indicated for transfer conveyor lock block 110 as it nears elastic conveyor 70.

Lock blocks 110, 112, 114 generally are similar to those previously described in regard to lock block 86 on timing belt 80. Referring to FIG. 1, a substantially wedge shaped cam 138 is disposed adjacent transverse conveyor 70 with a lower ramp or cam surface inclining downwardly on progressing toward conveyor 70. As an inner end portion of a lock block, such as that indicated at 110, moves along the surface of cam 138 its inner toothed element is urged into alignment with the side portions of the channel member in which it is mounted to open up the grooves therebetween allowing it to receive within such grooves elastic strands stretched between lock blocks 84, 86 and drums 74, 76.

The ramp surface of cam 138 ends a short distance beyond the path of the elastic strands held by lock blocks 84, 86 so that the transfer conveyor lock blocks, such as 110 snap tightly into locking positions to grasp the strands and hold them stretched therebetween.

Referring to FIGS. 3 and 4, the positions of a pair of laterally aligned transfer lock blocks 110, 110a at opposite sides of drum 30 are illustrated moving toward spaced apart portions of the reach of the elastic strands extending between lock blocks 84, 86 and drums 74, 76.

The lock blocks on the drum are spaced more closely together than drums 74, 76, and are able to engage and grasp elastic strands stretched between drums 74, 76.

Figure 3A:
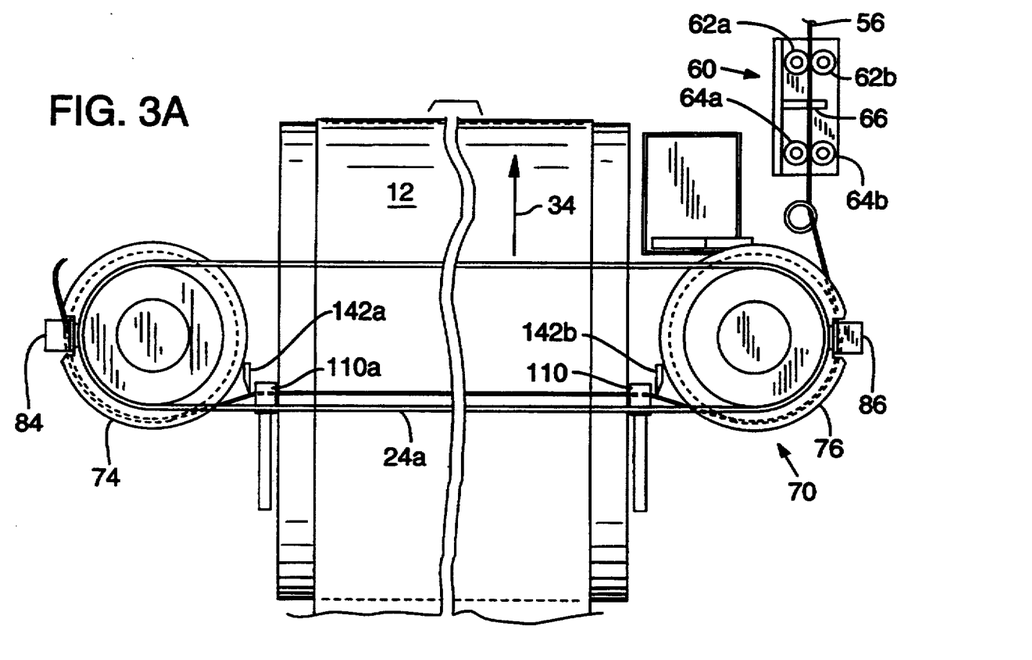

FIG. 3A illustrates lock blocks 110, 110a moved fully into grasping engagement with the elastic strands. At this point the lock blocks have closed to their locking positions and grip spaced regions of the elastic strands.

A pair of spaced cutters 142a, 142b are positioned laterally outwardly from the transverse conveyor lock blocks 110, 110a, such that as these lock blocks move the elastic strands in the direction of movement of the periphery of the drum, as indicated by arrow 34, the cutters sever the elastic strands from conveyor 70 whereby they may be carried in a tensioned condition by lock blocks 110, 110a from the position illustrated for lock block 110 in FIG. 1 around to the position illustrated for lock block 112. This causes the elastic strands to be laid against the outer surface of backing material 12.

The transfer conveyor lock blocks on the drum are spaced apart a distance greater than the width of the backing sheet to which they are to be applied. The lock blocks thus hold stretched therebetween what is referred to herein as a gross length of the elastic strands which is greater than the width of the material on which they are to be deposited.

An adhesive spray device indicated generally at 146 is positioned to spray a coating of adhesive material onto the elastic strand portions held between the lock blocks and onto the underlying backing material to secure the strands to the backing material. The adhesive spray is applied between, and not on the lock blocks, such that the lock blocks have minimum need for cleaning during operation.

As the transfer conveyor lock blocks on the drum carry the stretched elastic toward the top portion of the drum a pad 14 is placed on the backing sheet and a liner sheet 16 is placed atop the absorbent pad and backing sheet. This occurs generally adjacent the nip between rollers 30, 38. In FIG. 2, lock blocks 114, 114a are illustrated holding stretched sections of elastic extending across the drum between sheets 12, 16. These sheets and elastic strands are pressed tightly together between bumper 38a on roller 38 and drum 30.

In the position as shown in FIG. 2 the tensioned elastics are still in what is referred to herein as a gross length which is the full spacing between opposed lock blocks 114, 114a. This gross length is greater than the width of the product to be produced which in the illustrated embodiment is the width 12a of the backing and liner sheets being carried on the conveyor.

After the materials pass the nip between rollers 30, 38 a pair of cutters 150, 152 positioned closely adjacent opposite edges of the backing and liner sheets sever the elastic bands at the edges of the backing and liner sheets to produce a net length of elastic carried between the sheets. This net length is substantially equal to the width of the product carried by the conveyor.

Although not shown, a subsequent cam is provided to cause the transfer conveyor lock blocks to open and a current of air is directed thereagainst to remove waste sections of elastic held therein after severing by cutters 150, 152.

Describing operation of the apparatus in the production of garments, such as disposable diapers or training pants, backing sheet material 12 is carried substantially continuously along a flow path around a portion of the periphery of drum 30.

A previously scored strip of elastic material is drawn from a container, or reservoir, 54 and is carried through a splitter 60 which not only splits the strip into multiple strands, but also produces tension and stretch in the strands. These strands are carried into a position to be grasped by a lock block 84, or 86, and then carried with the lock block around drums 74, 76 on transfer conveyor 70. The elastic strands are carried substantially continuously in the direction of arrow 106 by the lock blocks and drums in a region, or reach, extending transversely of and spaced a short distance radially outwardly from the periphery of drum 30. The strands generally are aligned in a plane which extends substantially radially outwardly from the drum.

As drum 30 is rotated under power to carry backing material along the flow path the transfer lock blocks 110, 112, 114 rotate with the drum. The reaches of the elastic strands extending between drums 74, 76 and lock blocks 84, 86 are grasped by a pair of transfer conveyor lock blocks (as indicated in FIGS. 3, 3A) which have been opened by passage over wedge-shaped cams such as that indicated at 138.

Almost immediately after being received in the lock blocks the elastic strands are clamped therein and carried with the transfer conveyor lock blocks in the direction of flow of the backing sheet and against cutters 142a, 142b. The cutters sever the stretched region of elastic strands between the transfer conveyor lock blocks from remainder portions held by lock blocks 84, 86. Due to the elasticity of the material being operated on, and the substantially rapid grasping of the strands by the transfer conveyor lock blocks and moving them rapidly against the cutters there is no need to slow, or stop, the operation of the transverse conveyor 70 to allow pick up by the transfer conveyor lock blocks. The transverse conveyor 70 can operate substantially continuously to move tensioned elongate strands of elastic into position to be picked up by the transfer conveyor lock blocks.

After the gross length sections of stretched elastic have been grasped by the transfer conveyor lock blocks at opposite ends of the drum they are carried, still in a tensioned state, to a position adjacent an adhesive applicator 146 which sprays adhesive thereon. Due to the action of the eccentric cam 134 the lock blocks are laid over to a position tangent to the periphery of the drum, as is lock block 112, and the elastic strands are laid onto the surface of the underlying backing sheet as it is carried about the drum. The backing material with the stretched elastics placed thereon are carried to the position between rollers 30, 38. A pad 14 has previously been inserted in the space between liner sheet 16 and backing sheet 12. A series of elongate stretched elastics extending across the materials lead the pad on the conveyor and another series of stretched elastics follow the pad in the conveyor flow path.

After the combined sheets and pads have been assembled, cutters 150, 152 sever the elastic strands at the edge margins of the sheets to produce a net length of stretched elastic extending transversely of the moving series of interconnected garments.

In one form of the invention, and for example purposes only, the back sheet 12 carried in an elongate web through the assembly equipment may have a width in a range of approximately 12 to 15 inches. Similarly the liner sheet 16 carried as a substantially continuous web to be laid on the back sheet may have a width in the range of 12 to 15 inches. The absorbent pads 14 which are carried sequentially and in spaced relationship for insertion between the backing and liner sheets may have a length in the range of 16 to 20 inches and a width in a range of 3 to 12 inches. The absorbent pads have a substantially hourglass configuration as is illustrated in FIG. 2 and as is commonly known. The pads are spaced apart a distance in a range of 2 to 6 inches.

The drum 30 has a length of approximately 18 inches, such that its peripheral face is wider than the selected width of the backing and liner sheets. The diameter of drum 30 and the positioning of lock blocks, or grippers 110, 112, 114 thereon is such that proper spacing is provided between sets of elastic strands applied to the travelling web as illustrated in FIG. 2.

The elastic strands are stretched to approximately 3 times their normal at rest length as they are drawn through splitter 60 and about transverse conveyor 70.

The spacing between drums 74, 76 and lock blocks 84, 86 is approximately 24 inches, such that the tensioned reach of elastic extending therebetween and presented for transfer to the assembly is greater than the spaces between grippers at opposite ends of drum 30.

The spacing between opposed lock blocks carried on the rotating drum is approximately 18 inches. This distance is what is referred to as the gross length of tensioned elastic which is grasped and severed from the transverse conveyor to be carried to and placed on the backing sheet.

The cutters 150, 152 are spaced apart a distance substantially equal to the side-to-side width of the backing sheet 12, thus to sever the transversely applied elastics to a net length which substantially equals the width of the backing sheet and assembled materials.

Figure 8:
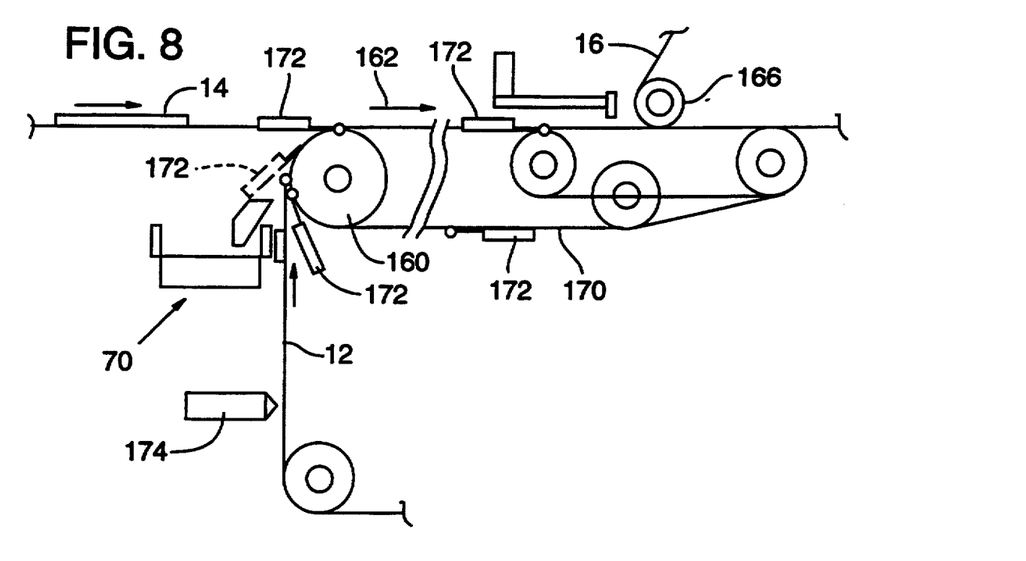
FIG. 8 is a somewhat schematic illustration of another embodiment of the invention.

Another embodiment of the invention is illustrated generally in FIG. 8. This embodiment is illustrated schematically only.

Referring to FIG. 8, an elongate web of backing material 12 is carried along a flow path which extends upwardly, then over a roller 160 and then continues to the right along a flow path indicated generally at 162. Absorbent pads 14 are also carried in the direction of flow path 162 and are placed atop sheet 12. A backing sheet 16 is carried about a roller 166 and placed on top of the absorbent pad 14 and sheet 12.

A transverse conveyor similar to that previously described generally at 70 is provided to stretch elongate strands of elastic transversely across a path spaced outwardly from and adjacent sheet 12. In this embodiment the guide drums and lock blocks, such as that indicated at 76 extend vertically and position the line of elastic strands held thereby substantially parallel to the upward path of sheet 12.

A pair of elongate, endless, flexible conveyor chains or belts such as that indicated generally at 170, are spaced laterally outwardly to opposite sides of the path of sheets 12, 16 and pad 14 and are trained about sprockets and rollers, whereby the upper reaches of the chains are substantially parallel to the upper portion of flow path 162. One portion of each of chains 170 is trained about a sprocket, or roller, similar to and aligned with roller 160.

Lock blocks 172 substantially similar to those previously described at 110, 112, 114 are secured to conveyor chains 170. These lock blocks are secured to the conveyor chains in such a manner that they are carried substantially tangent to the chains at all times. Thus, when the chain is travelling along a substantially straight reach, as on the top and bottom of the flow path, the lock blocks are substantially parallel to the conveyor chains. However, when the chain travels about a curved path, such as where it travels about roller 160, the lock block remains tangent to the chain, causing it to extend outwardly at a substantial angle relative to the curved member about which it is moving. Thus, the lock block 172 is positioned to pass through the space between drums 74, 76 on conveyor 70 to pick up reaches of elastic bands stretched therebetween. These bands then are severed to a gross length from the conveyor 70 and carried in the direction of flow path 162 with conveyor lock blocks 172. As the lock blocks reach the top of the flow path as indicated by arrow 162 they again lay flat against the path of material 12 to lay the tensioned elastics thereon.

An adhesive sprayer 174 is positioned to spray adhesive onto the outer surface of material 12 prior to tensioned elastic bands being placed thereon by lock blocks 172.

Figure 9:
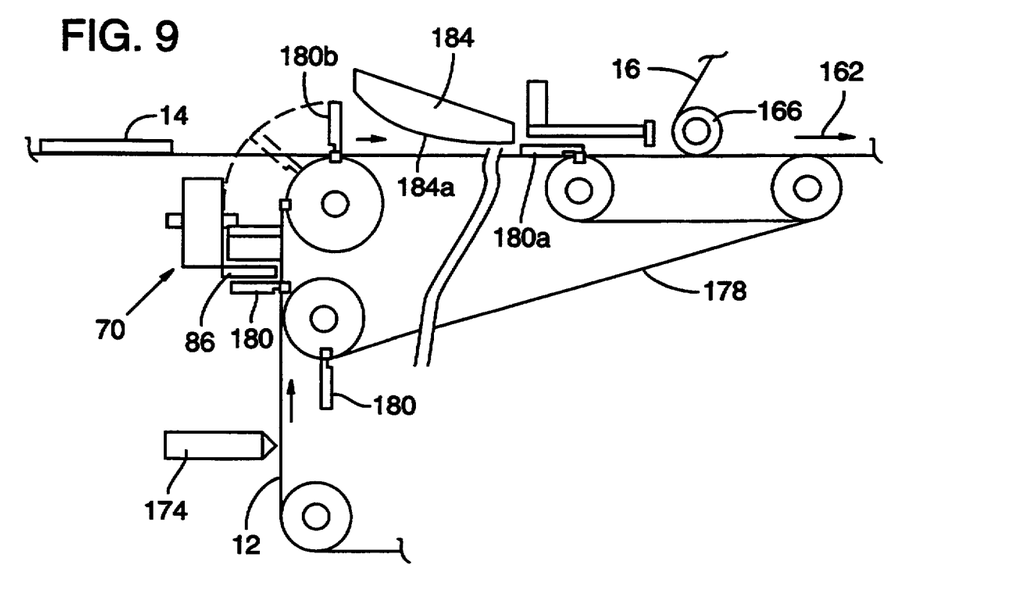
FIG. 9 is a somewhat schematic illustration of yet another embodiment of the invention.
Figure 10:
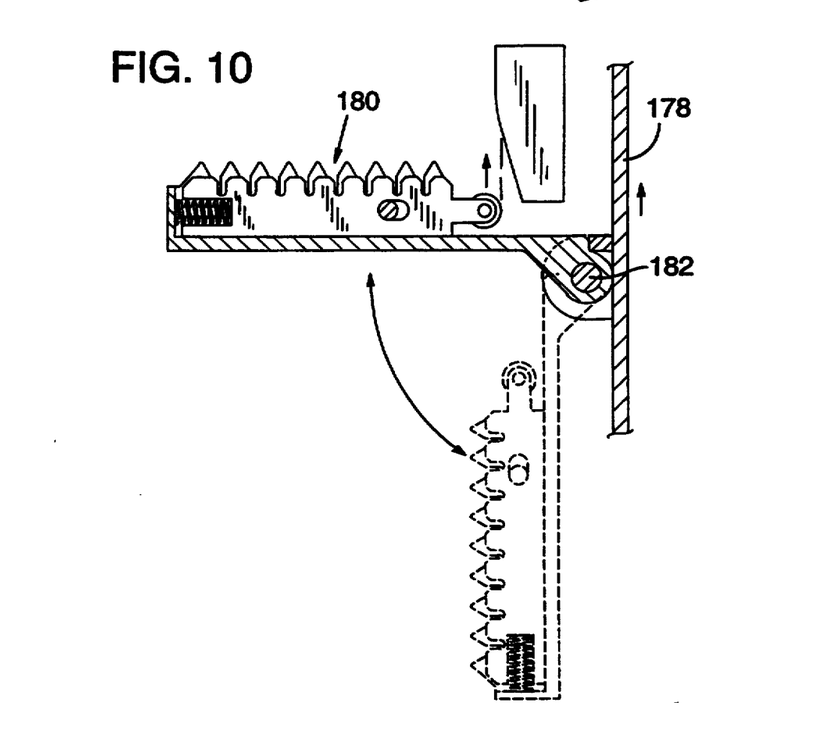
FIG. 10 is an enlarged illustration of an elastic gripper mounting in the FIG. 9 embodiment.

A third embodiment of the invention is illustrated in FIG. 9 and 10. Here, the backing sheet 12, liner sheet 16 and pads 14 are carried in substantially the same manner as set out above in relation to the FIG. 8 embodiment.

Transverse elastic conveyor 70 however, is positioned with the lock blocks and drum axes thereof extending horizontally, with a lock block 86 being indicated only schematically. Thus, the elastic strands extend transversely in a plane which lays substantially horizontally adjacent the backing sheet 12 which is moving upwardly therepast.

A pair of conveyor chains, or belts, 178 adjacent opposite sides of the path of the material carry lock blocks 180 similar to those previously described at 110, 112, 114. These are carried in such a manner that they normally extend outwardly substantially perpendicular to the chain on which they are carried, such that when they are adjacent conveyor 70 they are positioned to receive and grasp stretched reaches of elastic strands as previously described in relation to the first embodiment.

However, as is best illustrated in FIG. 10, the lock blocks are pivotally mounted for swinging about a pivot axis 182 relative to the conveyor chain 178 on which they are mounted. A torsion spring (not shown) holds them in position extending generally perpendicularly outwardly from their associated conveyor chain. The mounting allows them to be laid over against the conveyor chain as indicated generally in the position illustrated for lock block 180a in FIG. 9.

Overlying the flow path 162 in FIG. 9 is a cam 184, the underside 184a of which is operable to engage a lock block, such as that indicated at 180b approaching cam 184, and lay the lock block over to the position illustrated at 180a to press the elongate tensioned strands against the top surface of backing sheet 12 as it is carried along the flow path.

From the prior discussion, it will be seen that several embodiments of apparatus and methods are provided for carrying strands of tensioned elastic substantially transversely of the flow path of materials to which the elastic is to be applied and without hesitation of such materials permitting a transfer conveyor to grasp such strands, sever a gross length of elastic strand material therefrom while still in its tensioned stated, and carry such gross length strands into position to be placed and secured to material. Subsequent to placement of the elastic onto the material in a gross length (which is greater than the dimension of the material onto which it is placed), severing mechanism is operable to sever the tensioned elastic to a net length which is of a desired length relative to the material on which it is placed.

While preferred embodiments of the invention have been described herein, it should be apparent to those skilled in the art that variations and modifications are possible without departing from the spirit of the invention as set out in the following claims.

I claim:

1. A method for applying elongate tensioned elastic to material moving in one direction along a first flow path with the elastic extending transversely of the flow path, the method comprising the steps of moving said material in one direction along said flow path, providing a quantity of elongate elastic, drawing an elongate section of elastic from such quantity of elastic, stretching said section of elastic to a desired tension, moving said elastic in its tensioned state longitudinally and substantially continuously along a second flow path extending transversely of and spaced from said first flow path, grasping a portion of said section of elastic at spaced apart regions adjacent opposite sides of said flow path and, while maintaining tension in said elastic, moving it in the direction of said first flow path, cutting said section of elastic outside said spaced portions to sever the elastic from remainder portions drawn from the reservoir, and depositing said severed elastic on material carried along said first flow path.

2. The method of claim 1, which further comprises the step of applying adhesive to secure the elastic to the material.

3. The method of claim 1, wherein the steps of drawing, stretching and moving elastic comprises simultaneously drawing, stretching and moving multiple elongate strands of elastic, with said strands being moved substantially parallel to and spaced from each other to extend transversely of said flow path.

4. The method of claim 3, wherein said multiple elastic strands are disposed in a substantially common plane which on movement along said second flow path extends outwardly at a substantial angle from said first flow path, and in said depositing step said elastic strands are laid over in their substantially parallel spaced relation onto the material.

5. The method of claim 1, wherein said material has a selected width, said section of elastic is stretched to a length greater than said selected width, said grasped portion of the elastic being a gross length which is greater than said selected width, and following said depositing step said elastic is cut to a net length substantially equal to said selected width.

6. Apparatus for applying elongate tensioned elastic to material moving along a flow path with the elastic extending transversely of the flow path comprising, a first conveyor for carrying material in one direction along the flow path, elastic storage for holding a quantity of elongate elastic, a second conveyor operable to draw elastic from said storage, tension such elastic, and move the elastic longitudinally in a tensioned state substantially continuously along a region extending transversely of and spaced from said flow path, a pair of spaced transfer grippers movable along a path in said one direction, said grippers positioned to grasp spaced regions of the elastic held by the second conveyor adjacent opposite sides of said flow path, maintain the elastic in tensioned condition, and move it to said flow path to deposit the elastic on the material, and cutters positioned laterally outwardly of said grippers operable to sever the elastic from said second conveyor after it has been grasped by said grippers.

7. The apparatus of claim 6, which further comprises an adhesive applicator operable to apply adhesive to secure the elastic to the material.

8. The apparatus of claim 6, wherein said second conveyor comprises a pair of elastic holders spaced apart transversely of said flow path a distance greater than the spacing between said transfer grippers operable to hold a reach of tensioned elastic stretched therebetween and mechanism for moving said holders and elastic substantially continuously across said flow path.

9. The apparatus of claim 8, wherein said mechanism for moving said holders comprises an elongate endless flexible member having a reach extending transversely of said flow path on which said holders are mounted and drive mechanism for moving said flexible member with said reach thereof moving substantially continuously transversely of said flow path.

10. The apparatus of claim 8, wherein an elastic holder comprises mechanism defining a plurality of spaced apart holding bays each adapted to receive a portion of an elastic therein, a plurality of locking elements shiftable between lock positions operable to grasp elastics held in said bays and unlock positions, permitting elastic movement into or out of said bays, and biasing mechanism operable to yieldably bias said locking elements toward said lock positions.

11. The apparatus of claim 10, which further comprises mechanism operable to shift said locking elements to their unlock positions to permit elastic to enter a bay.

12. The apparatus of claim 8, wherein said second conveyor comprises a pair of drums spaced apart laterally of said flow path and said elastic holders are moved in a path to draw an elastic about a portion of the periphery of each drum as the elastic is moved by said second conveyor.

13. The apparatus of claim 12 wherein a drum has a peripheral groove formed therein to guide elastic as it is carried by said second conveyor.

14. The apparatus of claim 6, wherein said second conveyor comprises an elastic tensioning device operable to impart selected tension to elastic as it is moved by said second conveyor.

15. The apparatus of claim 6, wherein said first conveyor comprises a rotatable drum having a peripheral face on which material is supported for movement along the flow path, and said grippers are carried adjacent opposite ends of the drum.

16. The apparatus of claim 15, wherein said second conveyor is operable to carry a tensioned reach of elastic transversely of and adjacent the periphery of said drum and said grippers project radially outwardly adjacent opposite ends of the drum to grasp elastic held by said second conveyor.

17. The apparatus of claim 16, wherein said grippers are mounted for swinging between a first position extending radially outwardly adjacent opposite ends of said drum and a second position in a plane extending substantially tangent to the periphery of the drum, and which further comprises positioning mechanism operable to swing said grippers between said first position for grasping elastic held by said second conveyor and said second position to deposit elastic on material carried on the drum.

18. The apparatus of claim 17, wherein said mechanism for producing swinging of said grippers comprises a cam.

19. The apparatus of claim 6, which further comprises conveyor mechanism on which said transfer grippers are mounted for movement along and laterally outwardly of said flow path, said grippers being mounted for swinging from a first position extending outwardly said flow path to grasp elastic on said second conveyor to a second position contiguous the flow path to deposit elastic on material carried along said flow path.

20. The apparatus of claim 19, wherein said conveyor mechanism comprises a cam for shifting said grippers between said first and second positions.

21. The apparatus of claim 19, wherein said conveyor mechanism comprises a pair of substantially parallel endless elongate flexible members positioned adjacent opposite sides of said flow path having portions trained in paths paralleling the flow path to carry said grippers in gripper paths paralleling said flow path.

22. The apparatus of claim 21, wherein said grippers are pivotally mounted on said flexible members for swinging between said first and second positions.

23. The apparatus of claim 22, which further comprises biasing means yieldably urging said grippers to their first position and a cam operable to swing said grippers to their second position.

24. The apparatus of claim 21, wherein said flexible members are trained about curved guides in a region where said grippers pass adjacent said second conveyor, and said grippers comprise elongate members each of which is fixedly attached adjacent one of its ends to its associated flexible member to remain tangent to the path of said flexible member, such that when the flexible member travels around a curved path the gripper is disposed tangent to said curved path with portions of said gripper which are not attached to the flexible member extending outwardly at an angle from the flexible member and when the flexible member travels along a straight path the gripper is parallel to the flexible member.

25. Apparatus for applying elongate tensioned elastic to material moving along a flow path with the elastic extending transversely of the flow path comprising,
a first conveyor including a rotatable drum for carrying material on the peripheral face of the drum in one direction along the flow path,
elastic storage for holding a quantity of elongate elastic,
a second conveyor including an elongate endless flexible member having a reach extending transversely of and adjacent the periphery of the drum, a pair of spaced apart elastic holders mounted on the flexible member, and drive mechanism for moving said reach substantially continuously transversely of said flow path, said second conveyor being operable to draw elastic from said storage, tension such elastic, and move the elastic longitudinally in a tensioned state substantially continuously along a region extending transversely of and spaced from said flow path,
a pair of spaced elastic grippers movable along a path in said one direction, said grippers carried adjacent opposite ends of the drum and projecting outwardly therefrom to grasp spaced regions of the elastic held by the second conveyor adjacent opposite sides of said path, maintain the elastic in tensioned condition, and move it to said flow path to deposit the elastic on the material, and
cutters positioned laterally outwardly of said grippers operable to sever the elastic from said second conveyor after it has been grasped by said grippers.

26. The apparatus of claim 25, wherein said grippers are mounted for swinging between a first position extending radially outwardly adjacent opposite ends of said drum and a second position tangent to the periphery of the drum, and which further comprises positioning mechanism operable to swing said grippers between said first position for grasping elastic held by said second conveyor and said second position to deposit elastic on material carried on the drum.

27. Apparatus for applying elastic to material for garments comprising,
a first conveyor for carrying material of a selected width for a garment in one direction along a first flow path,
a second conveyor operable to carry a section of elastic longer than said selected width and held in tension substantially continuously along a second path extending transversely of and spaced from said first flow path,
a pair of laterally spaced transfer grippers operable to grip a portion of the section of elastic carried by the second conveyor, the transfer grippers being capable of gripping a gross length of elastic therebetween which is greater than said selected width, the gross length including a lesser net length of elastic between the transfer grippers which is substantially equal to the selected width,
a cutter operable to sever the elastic laterally outwardly of the transfer grippers after the transfer grippers have grasped the elastic, and
the transfer grippers being mounted for movement with the cut elastic in the first flow path direction and operable to deposit the cut elastic on material on the first conveyor.

28. The apparatus of claim 27, wherein the first conveyor and grippers move at substantially the same speed adjacent each other in the first flow path direction, and the transfer grippers are operable to deposit the cut elastic on the material.

29. The apparatus of claim 26, which further comprises an adhesive applicator operable to apply adhesive to elastic held between the transfer grippers.

30. The apparatus of claim 27, which further comprises a second cutter positioned to cut elastic held between the transfer grippers after the elastic is deposited on material on the first conveyor, the second cutter being operable to cut the elastic to said net length.

* * * * *